United States Patent [19]
Rom et al.

[11] Patent Number: 5,429,608
[45] Date of Patent: Jul. 4, 1995

[54] APPARATUS FOR REMOVING AN INDWELLING TUBE

[75] Inventors: Paul F. Rom, Kentwood; Russell A. Corace, Grand Rapids; Roderick E. Briscoe, Rockford, all of Mich.

[73] Assignee: DLP, Inc., Grand Rapids, Mich.

[21] Appl. No.: 228,713

[22] Filed: Apr. 18, 1994

Related U.S. Application Data

[62] Division of Ser. No. 81,788, Jun. 22, 1993, Pat. No. 5,364,366.

[51] Int. Cl.$^6$ .............................................. A61M 5/32
[52] U.S. Cl. ..................................... 604/163; 604/171
[58] Field of Search ............... 604/163, 171, 172, 263, 604/280, 283, 276

[56] References Cited

U.S. PATENT DOCUMENTS

| | | |
|---|---|---|
| 1,120,549 | 12/1914 | Schellberg . |
| 1,196,250 | 8/1916 | Kuhn . |
| 1,351,917 | 9/1920 | Kuhn . |
| 2,856,932 | 10/1958 | Griffitts . |
| 3,244,169 | 4/1966 | Baxter . |
| 3,709,223 | 1/1973 | Macalalad et al. . |
| 3,726,283 | 4/1973 | Dye et al. . |
| 3,742,960 | 7/1973 | Dye et al. . |
| 3,766,915 | 10/1973 | Rychlik . |
| 3,825,001 | 7/1974 | Bennet et al. . |
| 3,894,540 | 7/1975 | Bonner, Jr. . |
| 3,934,721 | 1/1976 | Juster et al. . |
| 3,967,728 | 7/1976 | Gordon et al. . |
| 4,140,127 | 2/1979 | Cianci et al. . |
| 4,227,533 | 10/1980 | Godfrey . |
| 4,230,115 | 10/1980 | Walz, Jr. et al. . |
| 4,392,853 | 7/1983 | Muto . |
| 4,772,275 | 9/1988 | Erlich . |
| 4,790,834 | 12/1988 | Austin . |
| 4,878,762 | 11/1989 | Uddo, Jr. et al. . |
| 4,887,615 | 12/1989 | Taylor . |
| 5,181,913 | 1/1993 | Erlich . |
| 5,336,193 | 8/1994 | Rom et al. ............... 604/171 |
| 5,364,366 | 11/1994 | Rom et al. ............... 604/163 |

*Primary Examiner*—John D. Yasko
*Attorney, Agent, or Firm*—Harris Beach & Wilcox

[57] ABSTRACT

An apparatus for the sanitary simultaneous removal of a plurality of indwelling tubes from an implantation site in a patient comprises a tube adapter that is connectable to the indwelling tubes. An impervious sleeve is fan-folded into a hub which extends around the tube adapter. In assembly the folded sleeve is retained by a shrink-wrapped plastic film. The sleeve can be extended for receiving the indwelling tubes therethrough and to encompass the implantation site. The indwelling tube and the implantation site are isolated from the environment when the distal open end of the sleeve is extended and applied about the implantation site and the indwelling tube is withdrawn into the sleeve. A drawstring is provided for closing the distal end of the sleeve after the tube has been withdrawn. The indwelling tubes can be maintained under suction or in connection with a drain during the removal operation.

19 Claims, 10 Drawing Sheets

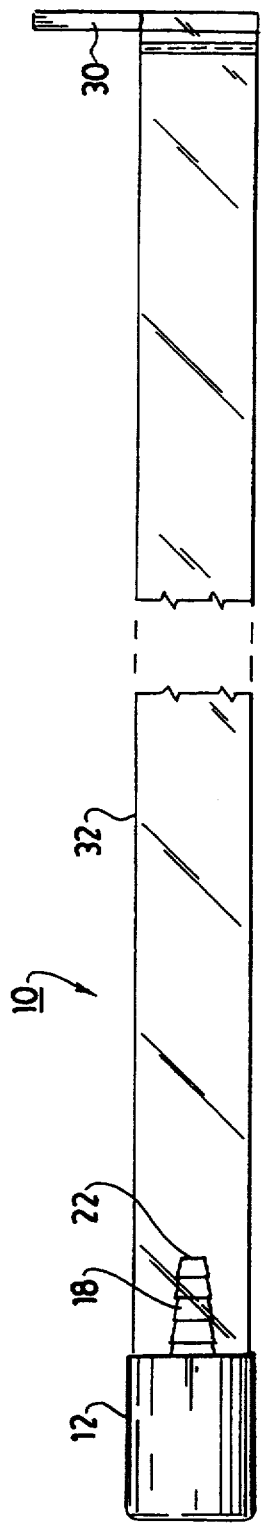
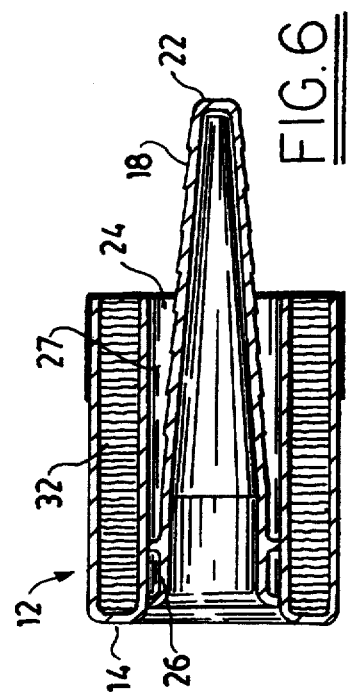
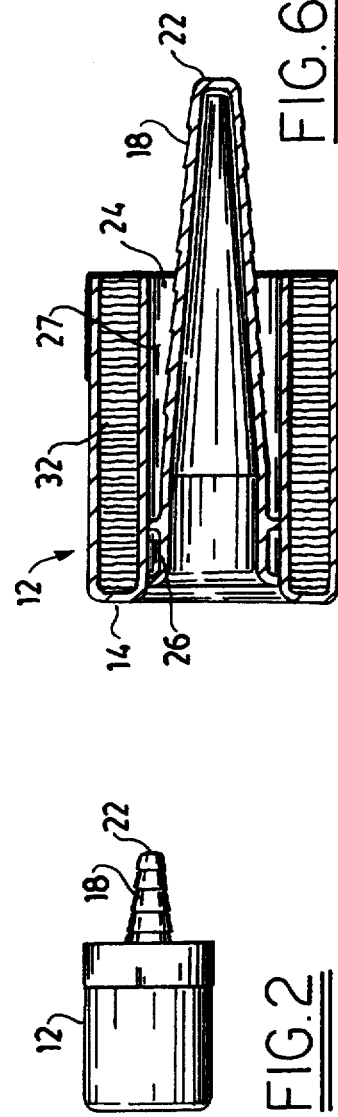
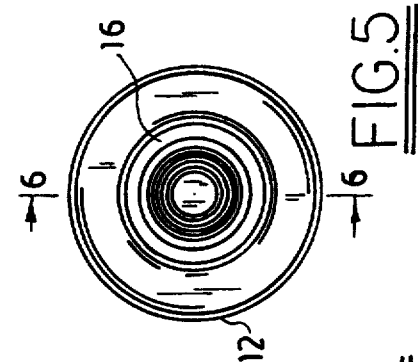
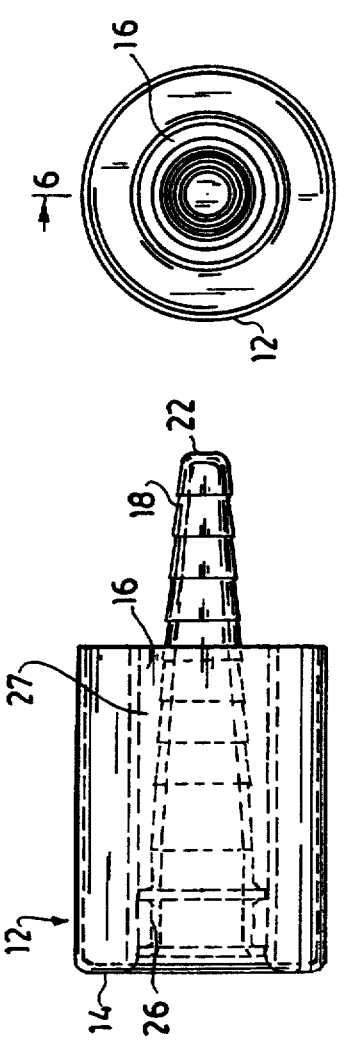

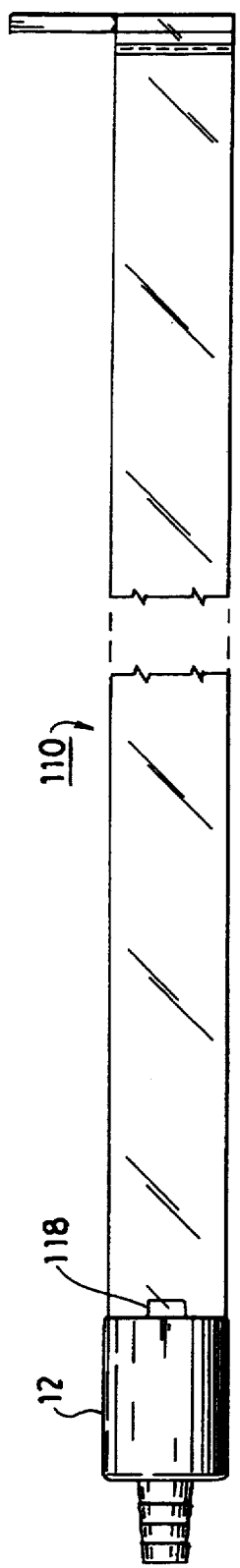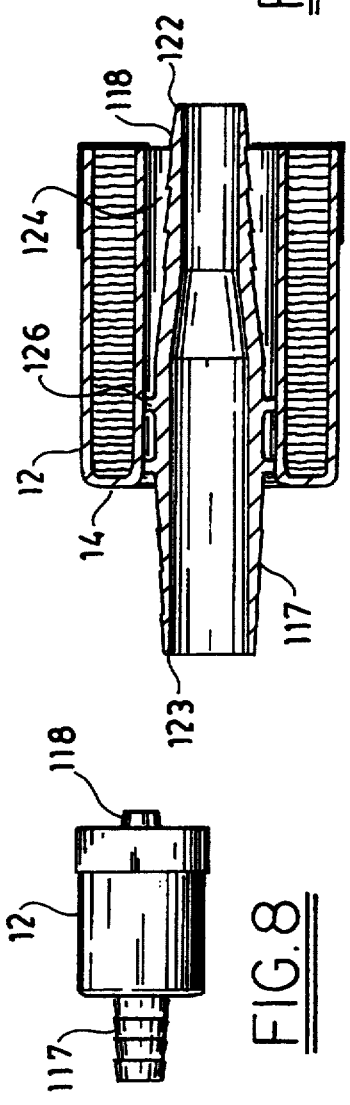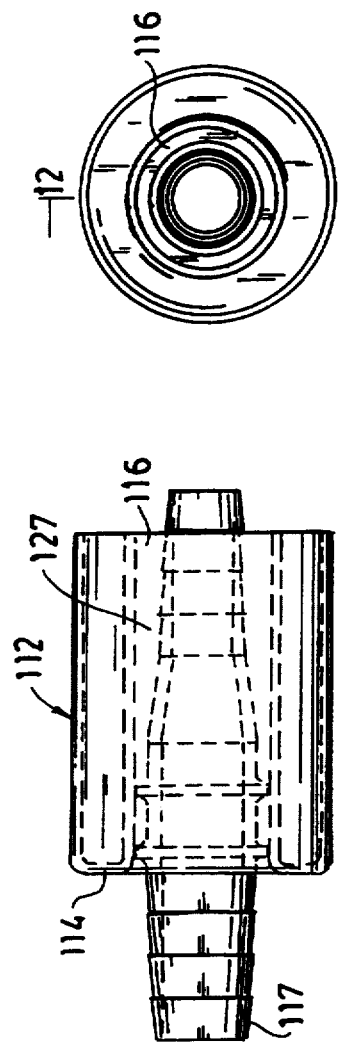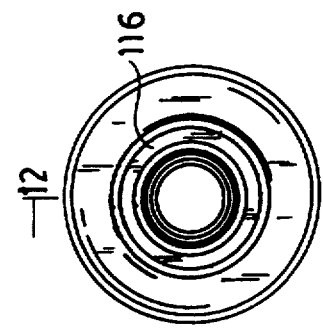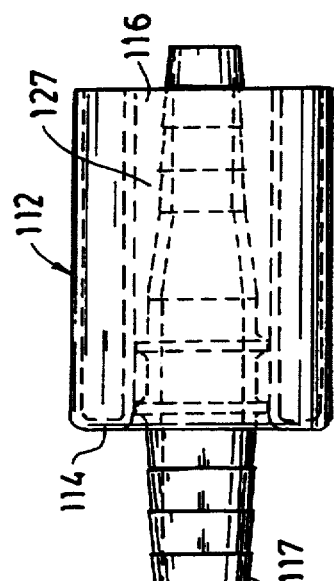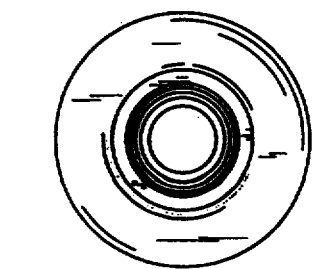

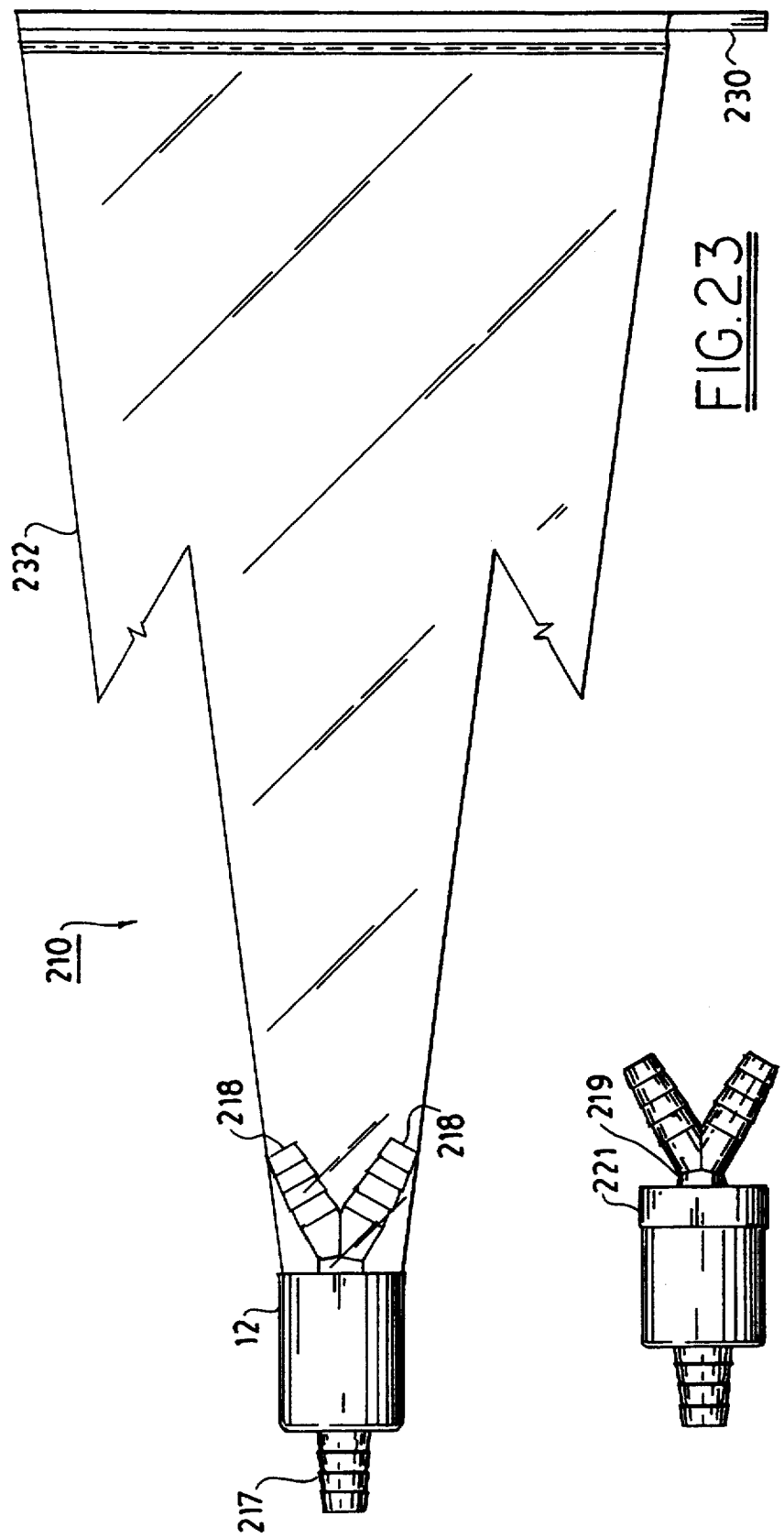

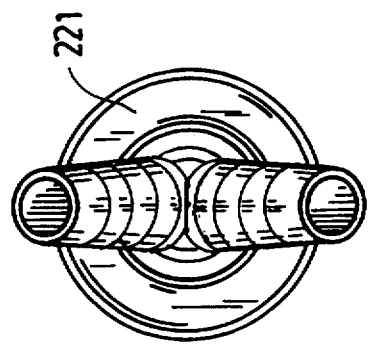
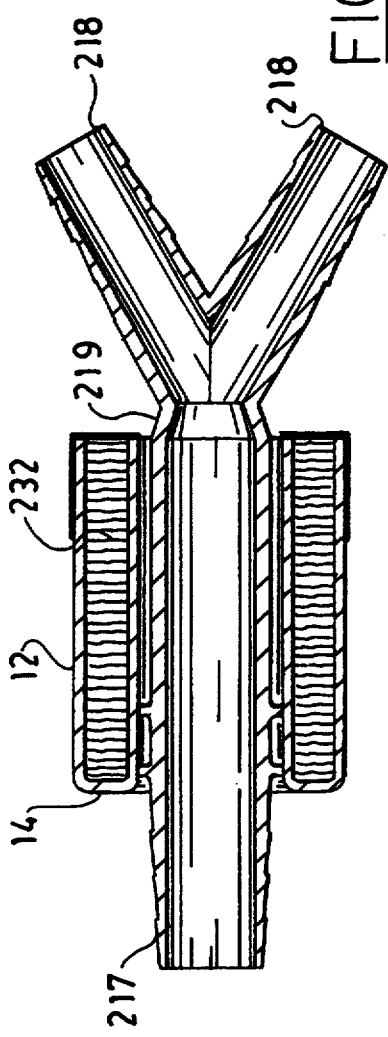
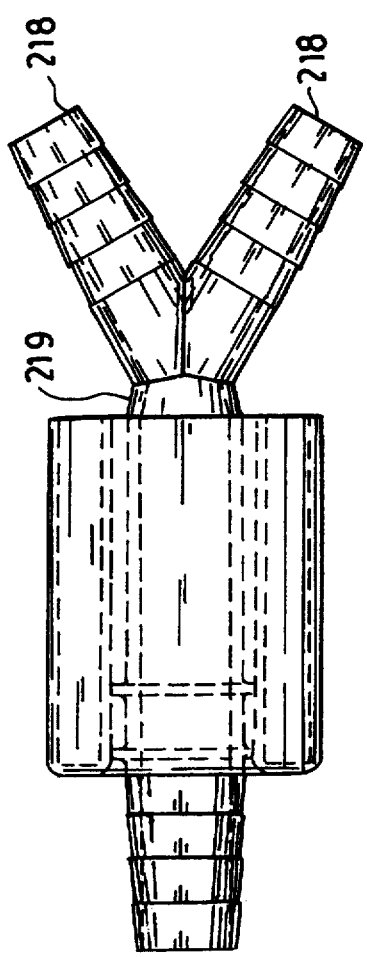
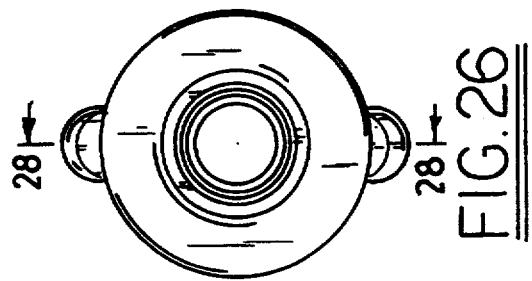

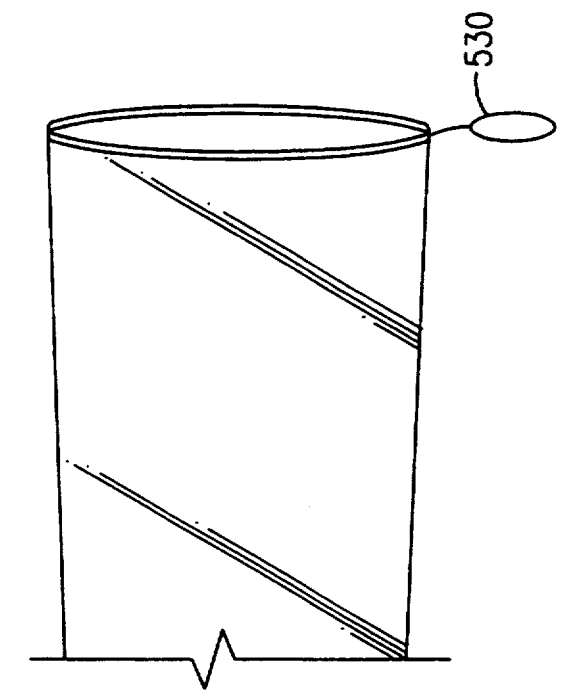
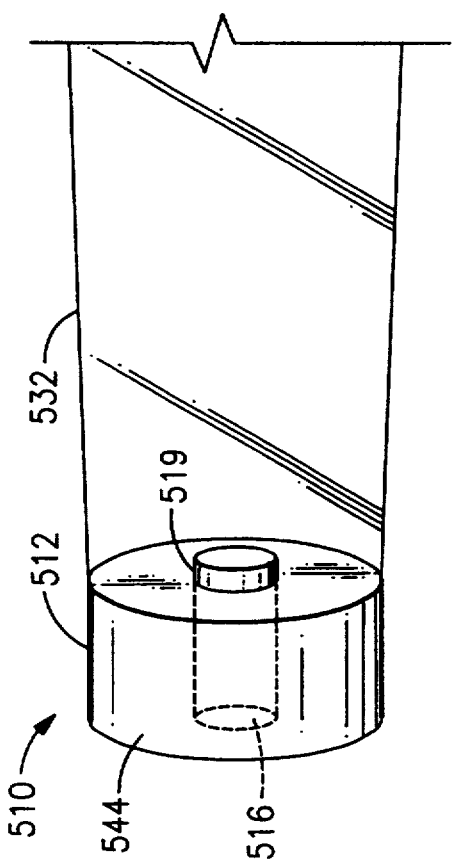
FIG.35
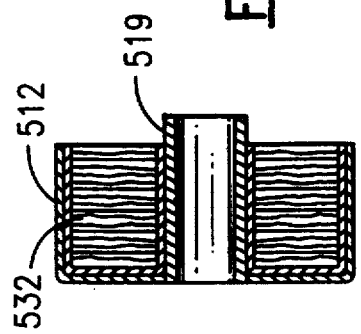
FIG.36

APPARATUS FOR REMOVING AN INDWELLING TUBE

This is a division of application Ser. No. 08/081,788, filed Jun. 12, 1993 now U.S. Pat. No. 5,364,366.

BACKGROUND OF THE INVENTION

1. Field of the Invention

This invention relates to the sanitary removal of tubes which are indwelling in the body of a patient. More particularly this invention relates to an apparatus for isolating an indwelling tube and its site of insertion while removing the tube, in order to protect the health care worker and the environment.

2. Description of the Prior Art

In recent years recognition has come that blood and body fluids, which carry pathogens such as bacteria and the hepatitis B and human immunodeficiency viruses, represent a serious threat to health care workers, and a general biohazard in the environment. Safety practices and health care regulations have accordingly been strengthened, and it now is standard practice for health care workers to employ universal precautions when working with potentially infectious patients, their blood, secretions, and other body fluids.

Indwelling tubes such as chest tubes, endotracheal tubes, nasogastric tubes, and various catheters are commonplace in modern patient care. These tubes are necessarily in contact with potentially hazardous blood and body fluids. When they are removed from the patient there is risk of contamination by direct contact with the exposed tube. Further biohazard is risked in consequence of blood and body fluids dripping from the tube, or flowing from a body orifice or an implantation site during its removal. Some tubes are notoriously difficult to control during removal, which can lead to spattering and spraying of infectious body fluids in the patient area, and even the formation of aerosols which pose a serious health risk to those nearby.

A device for removing monitoring tubes is disclosed in Uddo Jr. et al, U.S. Pat. No. 4,878,782 in which a tuba to be removed is received into the open mouth of a canister, and into the blind tip of a fully retracted sheath bonded thereto, after which the tube is pulled out of the patient, and the sheath drawn into full extension therewith. The canister is then capped, enclosing the tube for sanitary disposal. This system does not permit the tube to remain attached to a suction or drain hose during removal, as may be desirable in certain applications, because the tube's free and is immediately isolated prior to delivery from the patient.

SUMMARY OF THE INVENTION

It is therefore a primary object of the present invention to provide an improved apparatus for removing an indwelling tuba from a patient while preventing contact between the tube, the environment, and persons in the vicinity.

It is another object of the invention to provide a sealable unit for the sanitary disposal of a removed indwelling tube therein.

It is a further object of the invention to remove an indwelling tube in an aseptic manner.

It is yet another object to prevent contamination of the environment during the operation of removing an indwelling tube from a patient.

These and other objects of the present invention are attained by an apparatus for the sanitary removal of an indwelling tube from an implantation site in a patient, comprising a tube adapter having a distal end that is connectable to the indwelling tube. An impervious sleeve is folded around the tube adapter, the sleeve having a closed proximal end, and an open distal end for receiving the indwelling tube therethrough. The distal end is dimensioned to encompass the implantation site. The indwelling tube and the implantation site are isolated from the environment when the distal open end of the sleeve is extended and applied about the implantation site and the indwelling tube is withdrawn into the sleeve.

In accordance with an aspect of the invention, the apparatus further comprises a hub, disposed in sealing contact about the tube adapter, the hub having a container formed therein for containing the unextended sleeve. In accordance with another aspect of the invention, the container in the hub has an annular recess.

In accordance with yet another aspect of the invention, the sleeve is fan-folded within the annular recess, and is retained therein by a plastic film.

In accordance with still another aspect of the invention, the hub further comprises an annular container for containing a portion of the folded sleeve, the annular container having a central aperture therethrough, and a rim in opposing contact with the hub about the annular recess to encase the folded sleeve therebetween. The distal end of the sleeve is attached to the annular container for extension therewith about the indwelling tube.

A drawstring is provided for closing the distal end of the sleeve.

According to another aspect of the invention, the tube adapter is branched and can connect to a plurality of indwelling tubes.

In accordance with yet another aspect of the invention, a fluid communication path is established between a first tube adapter and a second tube adapter which are disposed on opposite sides of the hub. The first and second tube adapters are connectable to the indwelling tube and an external drainage tube respectively.

BRIEF DESCRIPTION OF THE DRAWINGS

For a better understanding of these and other objects of the present invention, reference is made to the detailed description of the invention which is to be read in conjunction with the following drawings, wherein:

FIG. 1 is a side elevation of a tube removal device in accordance with the invention with the sleeve extended;

FIG. 2 is a side elevation of the device shown in FIG. 1 with the sleeve collapsed therein;

FIG. 3 is an enlarged detail of the device of FIG. 2;

FIGS. 4 and 5 are rear and front elevations of the device of FIG. 2 respectively;

FIG. 6 is a sectional view taken through line 6—6 of FIG. 5;

FIG. 7 is a side elevation of a tube removal device in accordance with a first; alternate embodiment of the invention with the sleeve extended;

FIG. 8 is a side elevation of the device shown in FIG. 7 with the sleeve collapsed therein;

FIG. 9 is an enlarged detail of the device of FIG. 8;

FIGS. 10 and 11 are rear and front elevations of the device of FIG. 8 respectively;

FIG. 12 is a sectional view taken along line 12—12 of FIG. 11;

FIG. 23 is a side elevation of a third alternate embodiment of the invention with the sleeve extended;

FIG. 24 is a side elevation of the device shown in FIG. 23 with the sleeve collapsed therein;

FIG. 25 is an enlarged detail of FIG. 24;

FIGS. 26 and 27 are rear and front elevations of the device of FIG. 24 respectively;

FIG. 28 is a sectional view taken along line 28—28 of FIG. 26;

FIG. 35 is a perspective view of a fifth alternate embodiment of the invention with the sleeve extended; and FIG. 36 is a side elevation of the device of FIG. 35 with the sleeve packaged therein.

DESCRIPTION OF THE PREFERRED EMBODIMENT

Figure 13:
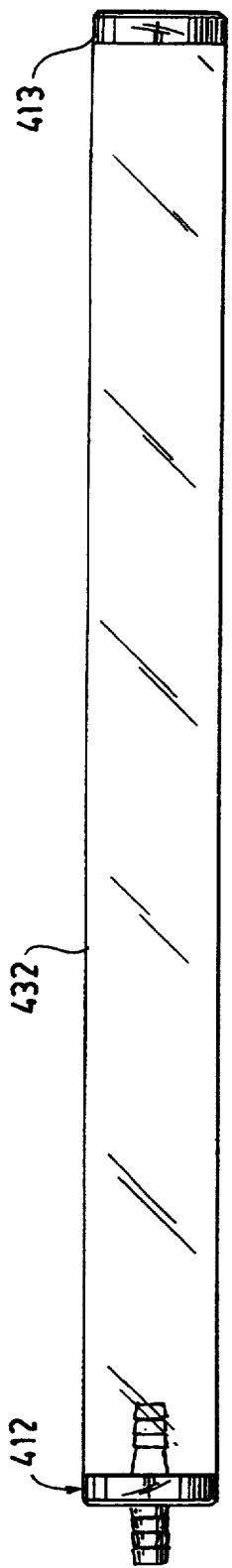
FIG. 13 is a side elevation of a tube removal device in accordance with a second alternate embodiment of the invention with the sleeve extended.
Figure 14:
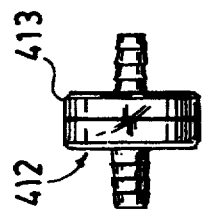
FIG. 14 is a side elevation of the device shown in FIG. 7 with the sleeve collapsed therein.
Figure 18:
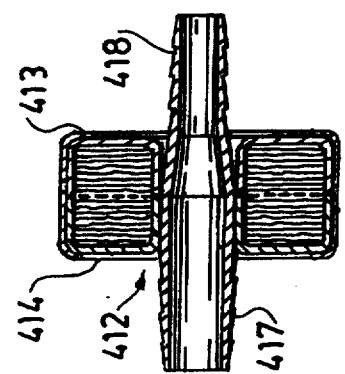
FIG. 18 is a sectional view taken along line 18—18 of FIG. 16.
Figure 17:
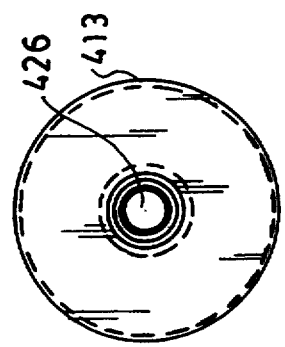
FIGS. 16 and 17 are rear and front elevations of the device of FIG. 14 respectively.
Figure 15:
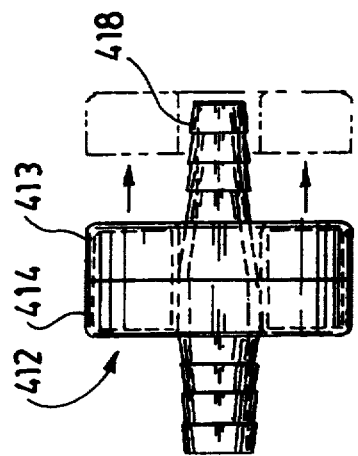
FIG. 15 is an enlarged detail of FIG. 14.
Figure 16:
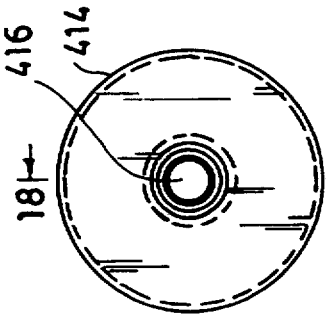
Figure 19:
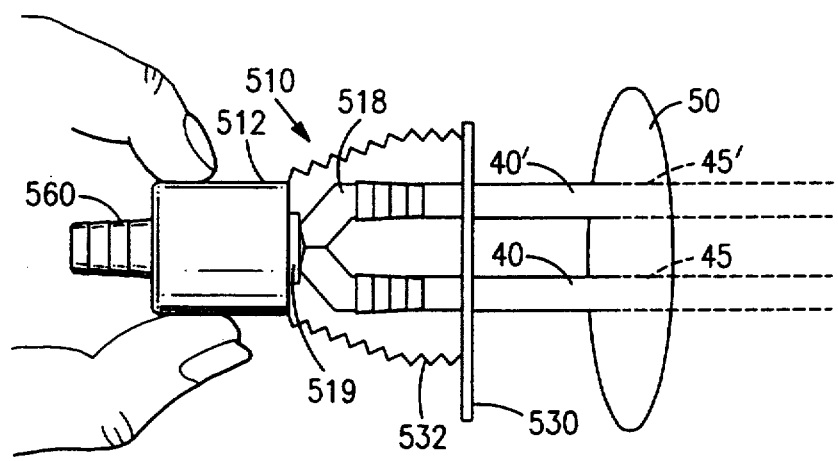
FIGS. 19–22 illustrate steps in the sanitary removal of an indwelling tube utilizing the device shown in FIG. 1.

In FIGS. 35–36 there is shown a preferred embodiment of a tube removal device 10 in accordance with the invention. A central hub 512, fabricated from polyethylene or other suitable material by injection molding or other well-known techniques, comprises an annular container portion 514 that encloses a central aperture 516. conventional hollow tube adapters (not shown) are insertable into the aperture 516 either through distal portion 519, or the proximal side of the hub 512.

Container portion 514 is occupied by a sleeve 532 of fan-folded flexible plastic material such as polyethylene sheet. One end of sleeve 532 is sealably bonded to container 514. Sleeve 532 can be unfolded to extend from hub 12 to form a sleeve as shown in FIG. 35. Drawstring 530 is provided at the free end of sleeve 32, and when it is pulled tight a chamber is defined by sleeve 32, and container portion 514. When aperture 516 is plugged the interior of the chamber becomes isolated from the environment.

Figure 20:
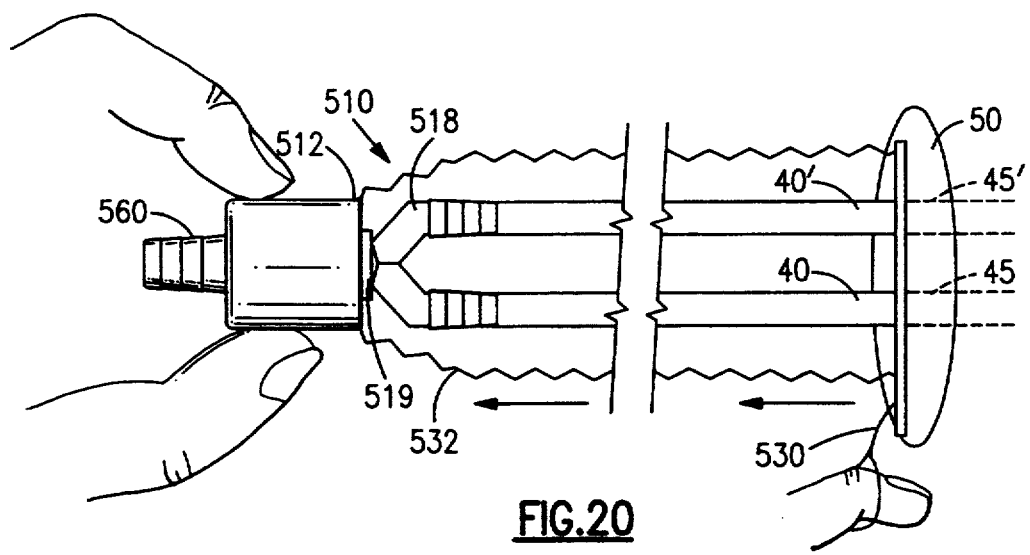
Figure 21:
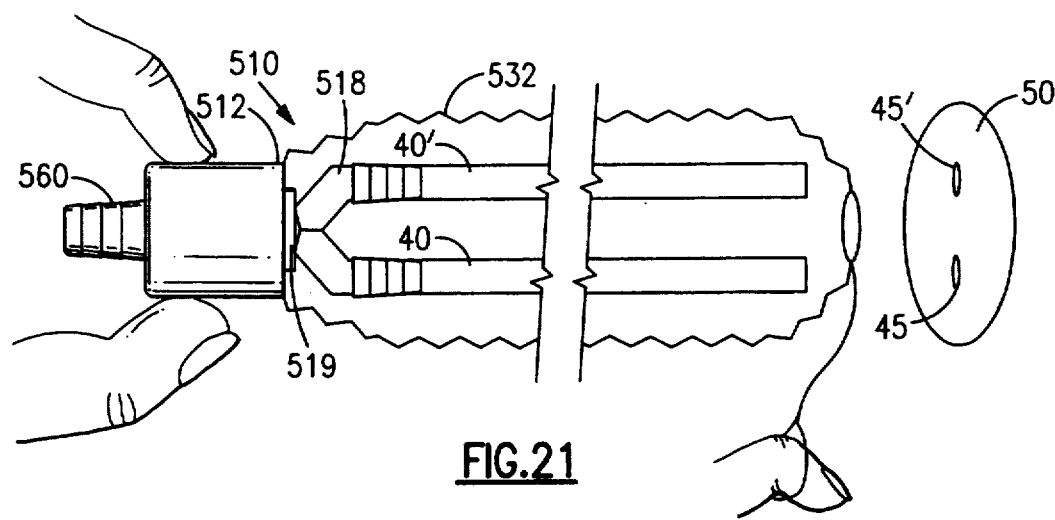
Figure 22:
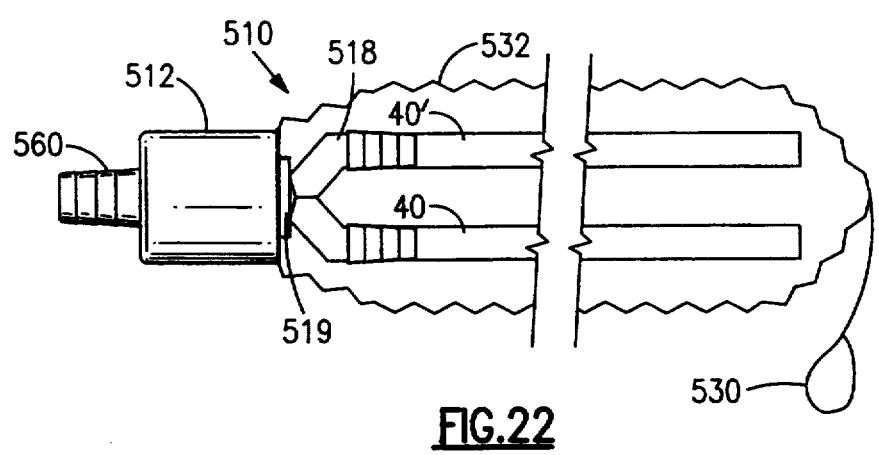

To understand how to use device 510 reference may be had to FIGS. 19–22, in which there is shown indwelling chest tubes 40, 40' which have been implanted through sites 45, 45' of the body of a patient 50, and are required to be removed in a sanitary manner. A conventional barbed Y-adapter 518 is snugly inserted into the ends of the chest tubes 40, 40' Prior to connecting the proximal end of the Y-adapter 518 to the tubing 560 of the closed wound drainage system, the device 510 is slipped over the tubing with the open end of the hub facing the Y-adapter 518. A shrink wrap (not shown) remains intact until the operator is ready to remove the chest tubes 40, 40'. The tubing 560 is then attached to the proximal end of the Y-adapter 518. As the branches of adapter 518 are barbed, the indwelling tubes 40, 40' cannot readily slip off during withdrawal. At the time of tube removal, the hub 512 is slid along the drainage tubing 560 to engage the proximal end of the Y-adapter. The shrink wrap is removed, and the sleeve 532 is withdrawn from the hub 512. Sleeve 532 is then extended over adapter 518 and indwelling tubes 40, 40', advanced up to the tube exit sites 45, 45', and brought into contact with the body surface of patient 50 to encompass the exit sites 45, 45'. By slipping a retaining finger and thumb through the drawstring 530, the health care worker can maintain the free end of sleeve 532 in contact with the body surface of the patient, as best seen in FIG. 20. Hub 512 is then pulled away from the patient to further extend the sleeve 532 and at the same time withdraw the indwelling tubes 40, 40' inside the sleeve. It will be appreciated that while the tubes are being withdrawn into the sleeve, the exterior portions of the tubes 40, 40' and the surgical implantation sites 45, 45' are enclosed within a sealed compartment and completely isolated from the environment. The sleeve is suitably dimensioned to completely contain the tubes when fully extended, as shown in FIG. 21. At this point it may be expedient to place a gauze or the like (not shown) over the surgical sites 45, 45'. By continuing to withdraw the hub 512 away from the patient and simultaneously maintaining traction on drawstring 530, the free end of sleeve 532 is sealed shut. In FIG. 22 the device 510 with the extracted tubes 40, 40' now completely enclosed therein is ready for disposal.

In the discussion of the alternate embodiments which follows, components which are unchanged from the first embodiment are indicated by the same reference numerals. All of them are preferably packaged in a shrink wrapped film, and are used in a similar manner.

In FIGS. 23–28 there is shown a first alternate embodiment, indicated generally by reference numeral 210 in FIG. 23, which is also adapted to the removal of two proximately disposed indwelling tubes in one operation. The construction is generally similar to that of the first embodiment, except that the adapter for external connection 217 and tube adapters 218, 218 are integral with the hub. The adapters 218, 218 are bifurcated at a point 219, both branches being in fluid communication with proximal tube adapter 217. Sleeve 232, fan-folded into container 14 as before, expands into a broad frustoconical chamber sufficient to clear the outwardly projecting adapters 218, 218, and to encompass two indwelling tubes and their respective implantation sites (not shown). Drawstring 230 i s lengthened appropriately to accommodate the greater dimension of the free end of the sleeve. Sleeve 232 is normally retained in container 14 by a shrink-wrapped plastic film 221 which folds over a portion off the exterior surface of hub 12. This film is removed prior to using the device. The procedure for operating this version is similar to the foregoing. The proximal adapter 217 can be connected to an external drain tube as before, so that at no time is the closed wound drainage system interrupted by the use of the device.

Turning now to FIGS. 7–12 there is shown a second alternate embodiment. This version is similar to the previous embodiment, except now a single, non-branched tube adapter 118 has a patent distal end 122, and is extended proximally beyond the hub 12 and configured to form a second tube adapter 117, also having a patent proximal tip 123. The tube adapters 117, 118 are thus in fluid communication. When using this embodiment, tube adapter 117 is first connected to an external drain tube (not shown), or optionally to a suction pump. Otherwise, the tube removal proceeds much as described for the first embodiment. Once the indwelling tube has been removed, the product and tube can be disposed of.

Figure 29:
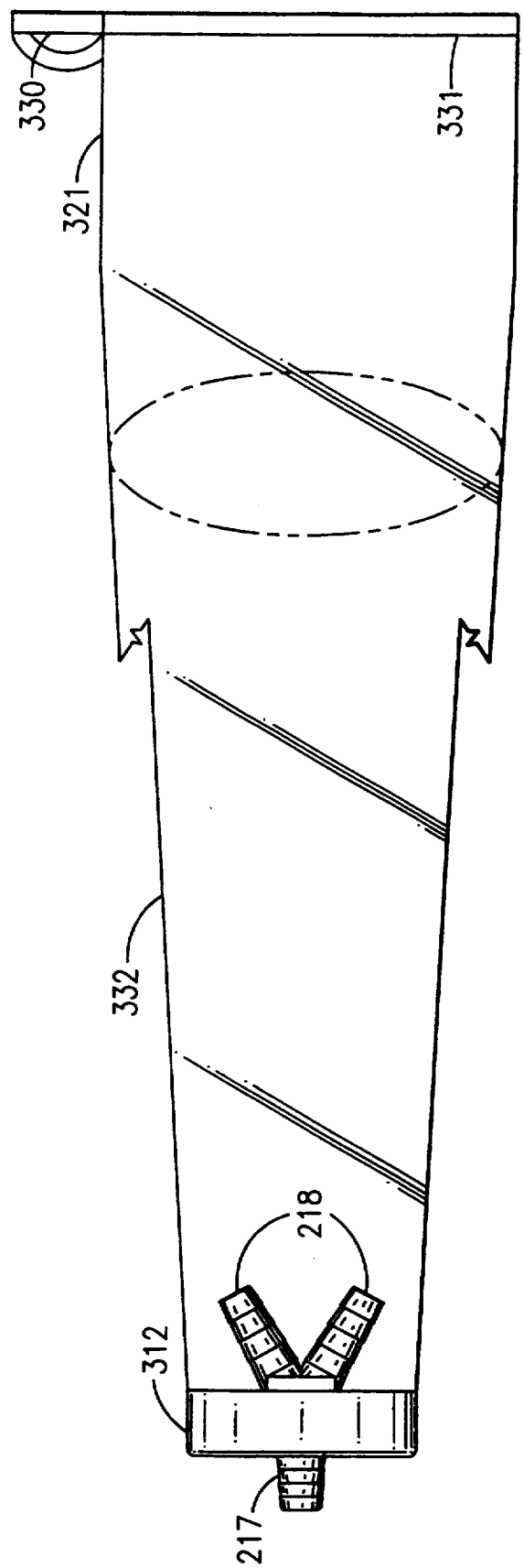
FIG. 29 is a side elevation of a fourth alternate embodiment of the invention with the sleeve extended.
Figure 30:
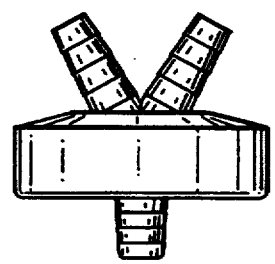
FIG. 30 is a side elevation of the device shown in FIG. 29 with the sleeve collapsed therein.
Figure 31:
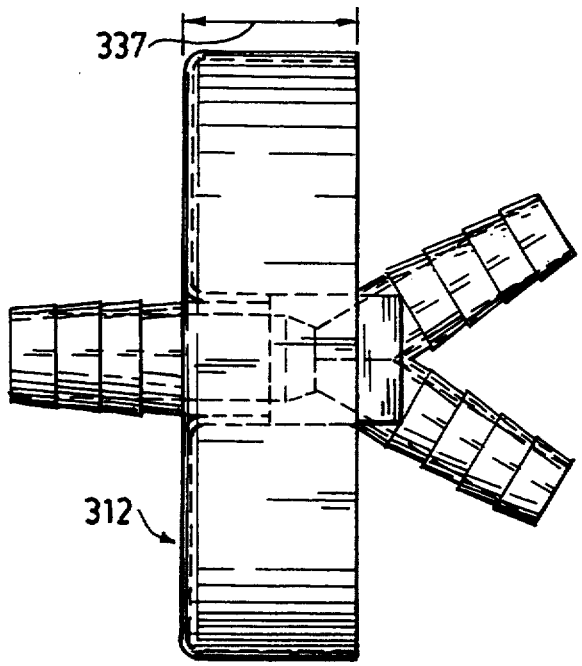
FIG. 31 is an enlarged detail of FIG. 30.
Figure 32:
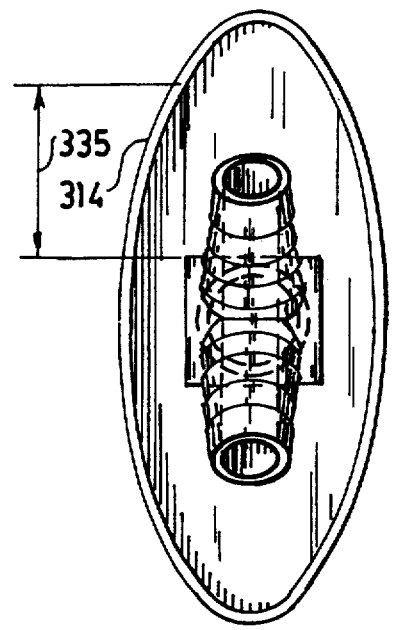
FIGS. 32 and 33 are front and rear elevations of the device of FIG. 31 respectively.
Figure 33:
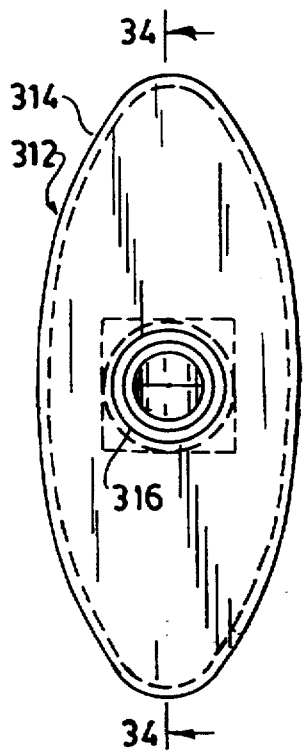
Figure 34:
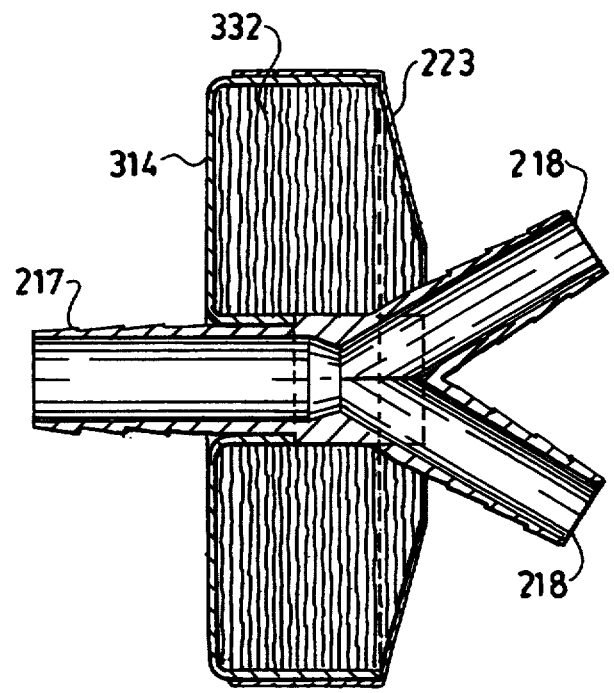
FIG. 34 is a sectional view taken along line 34—34 of FIG. 33.

A third alternate embodiment is illustrated in FIGS. 29-34, wherein the extended plastic sleeve 332 is elongated in an axis so that it has an oval cross section, yet remains trapezoidal in profile, as best seen in FIG. 29. In this variant, hub 312, and container portion 314 thereof are also elongated, so that they are oval in cross section. The maximum width dimension 335 of container portion 314 is considerably enlarged, while its height dimension 337 is relatively reduced from the preceding embodiments. Central aperture 316 remains circular in section. This embodiment is well adapted to the simultaneous removal of two indwelling tubes that are spaced apart a relatively greater distance.

In FIGS. 1-6 there is shown a fourth alternate embodiment of a tube removal device 10 in accordance with the invention. A central hub 12, fabricated from polyethylene or other suitable material by injection molding or other well-known techniques, comprises an annular container portion 14 that encloses a central aperture 16. A hollow barbed tube adapter 18 is disposed in the central aperture 16 with its distal end 22 protruding thereout, and its proximal portion 26 bonded to the inner wall 24 of the container portion 14 to form an annular seal therebetween. A sealed recess 27 is thus defined. The distal end or tip 22 of adapter 18 is also sealed. In practice the hub 12 and tube adapter 18 can be integrally molded.

As best shown in FIGS. 1 and 6, container portion 14 is occupied by a sleeve 32 of fan-folded flexible plastic material such as polyethylene sheet. One end of sleeve 32 is sealably bonded to container 14. Sleeve 32 can be unfolded to extend from hub 12 to form a sleeve as shown in FIG. 1. Drawstring or drawtape 30 is provided at the free end of sleeve 32, and when it is pulled tight a sealed chamber, isolated from the environment, is defined by sleeve 32, container portion 14, recess 27, and the sealed end 22 of tube adapter 18.

Turning now to FIGS. 13-18, there is shown a fifth alternate embodiment in accordance with the invention. In this version hub 412, constructed in the same general manner as in the preceding embodiment, is supplemented by a detachable annular container 413 having a central aperture 426 which receives the distal tube adapter 418. In assembly the sleeve 432 is fan folded into both containers, and the rims of container portion 414 of hub 412 and of container 413 oppose one another to fully contain the sleeve 423, which is bonded to both of them. In this embodiment the aperture 426 is dimensioned to pass over the free end of an indwelling tube. To use the device container 413 is separated from hub 412 and pulled away to unfold and extend the sleeve 432. The free end of an indwelling tube to be removed is passed through aperture 426, and the container 413 brought into contact with the body surface about the implantation site, carrying sleeve 432 therewith. Distal tube adapter 413 is then inserted into the free end of the indwelling tube, and the tube withdrawn while maintaining sealing contact between the body surface and container 413. Once the indwelling tube is safely encased within the sleeve and has completely passed through aperture 426, the aperture can be sealed or plugged.

While this invention has been explained with reference to the structure disclosed herein, it is not confined to the details set forth and this application is intended to cover any modifications and changes as may come within the scope of the following claims:

What is claimed is:

1. An apparatus for the sanitary removal of indwelling tubes from an implantation site in a patient while isolating the tubes and the implantation site from an environment thereabout, comprising:
   a tube adapter having a means disposed on a distal end thereof for connection to a plurality of indwelling tubes;
   an extensible impervious sleeve folded around said tube adapter, said sleeve having a closed proximal end, and further having an open distal end for receiving the indwelling tubes therethrough, said distal end being dimensioned to encompass the implantation site; and
   a hub, disposed in sealing contact about said tube adapter, said hub having means for containing said unextended sleeve;
   whereby said sleeve isolates the indwelling tubes and the implantation site from the environment when said distal open end of said sleeve is applied about the implantation site and the indwelling tubes are withdrawn into said sleeve.

2. The apparatus according to claim 1, wherein said means for containing comprises an annular recess formed in said hub.

3. The apparatus according to claim 2, wherein said sleeve is fan-folded within said annular recess, and further comprising means for retaining said sleeve therein.

4. The apparatus according to claim 3, wherein said hub further comprises an annular container for containing a portion of said folded sleeve, said annular container having a central aperture therethrough, a rim of said annular container being in opposing contact with said hub about said annular recess to encase said folded sleeve therebetween, said distal end of said sleeve being attached to said annular container for extension therewith about the indwelling tube.

5. The apparatus according to claim 1, further comprising a drainage adapter in communication with said tube adapter.

6. The apparatus according to claim 1, further comprising means for closing said distal end of said sleeve.

7. The apparatus according to claim 6, wherein said means for closing comprises a drawstring.

8. The apparatus according to claim 6, wherein said means for closing comprises a drawtape.

9. A method for the sanitary removal of a plurality of indwelling tubes from an implantation site in a patient while isolating the tubes and the implantation site from an environment thereabout, comprising the steps of:
   folding an extensible impervious sleeve into a hub that surrounds a tube adapter in sealing contact therewith, said sleeve having a closed proximal end, and further having an open distal end for receiving the indwelling tube therethrough, said distal end being dimensioned to encompass the implantation site, said tube adapter being simultaneously connectable to a plurality of indwelling tubes to be removed;

connecting said tube adapter to the indwelling tubes;

extending said sleeve about the indwelling tubes into sealing contact with the patient to encompass the implantation site; and while maintaining said distal end of said sleeve in sealing contact with the patient, performing the steps of:

removing said hub in a direction away from the patient to further extend said sleeve; whereby the connected indwelling tubes are simultaneously withdrawn from the patient into said sleeve; and sealing said distal end of said sleeve to completely enclose the withdrawn indwelling tubes therein.

10. The method of claim 9, wherein said step of sealing is performed by maintaining traction on a drawstring.

11. The method of claim 9, wherein said step of sealing is performed by maintaining traction on a drawtape.

12. An apparatus for the sanitary removal of a plurality of indwelling tubes from a patient, comprising:

a hub having a passage therethrough for establishing a fluid communication path between a first tube adapter and a second tube adapter, said first and second tube adapters being disposed on opposite sides of said hub, said first tube adapter being simultaneously connectable to a plurality of indwelling tubes, said second tube adapter being connectable to an external drainage tube;

an extensible sleeve having a closed proximal portion disposed about said first tube adapter and having an open distal end for receiving the indwelling tubes therethrough, said distal end being dimensioned to encompass an implantation site of the indwelling tubes, the indwelling tubes and the implantation site being isolated from an environment when said distal end is sealably applied about the implantation site, said hub comprising a container for said sleeve when said sleeve is unextended;

whereby the isolated indwelling tubes can be delivered from the patient into said sleeve.

13. The apparatus according to claim 12, wherein said hub comprises a container for said unextended sleeve therein.

14. The apparatus according to claim 13, further comprising means for retaining said sleeve in said container.

15. The apparatus according to claim 14, wherein said means for retaining comprises a plastic film.

16. The apparatus according to claim 12, further comprising means for closing said distal end of said sleeve after withdrawal of said tubes therein.

17. The apparatus according to claim 16, wherein said means for closing comprises a drawstring.

18. The apparatus according to claim 16, wherein said means for closing comprises a drawtape.

19. The apparatus according to claim 12, wherein said first tube adapter comprises a Y-adapter for connection with two indwelling tubes.

* * * * *